United States Patent [19]
Kawahara et al.

[11] Patent Number: 5,543,522
[45] Date of Patent: Aug. 6, 1996

[54] PROCESS FOR PREPARING AN AMBIENT TEMPERATURE MOLTEN SALT USING THIONYL CHLORIDE

[75] Inventors: Takayuki Kawahara; Hitoshi Suzuki; Asao Kominato, all of Ami-machi, Japan

[73] Assignees: Mitsubishi Chemical Corporation; Nisshin Steel Co., Ltd., both of Tokyo, Japan

[21] Appl. No.: 295,422

[22] Filed: Aug. 25, 1994

[30] Foreign Application Priority Data

Aug. 25, 1993 [JP] Japan .................... 5-210607
Aug. 25, 1993 [JP] Japan .................... 5-210608

[51] Int. Cl.$^6$ .................... C07F 5/06; C07D 213/18; C07D 233/90; B65D 85/18; C25D 21/18
[52] U.S. Cl. .................... 546/2; 546/9; 546/341; 546/272.7; 548/101; 548/337.1; 556/170; 564/291; 564/296; 568/9; 205/291; 205/292; 205/296; 205/297; 205/298; 106/1.22; 106/1.25; 423/635
[58] Field of Search .................... 546/2, 9, 278, 546/347; 548/101, 337.1; 564/291, 296; 556/170; 423/635; 265/291, 292, 296, 297, 288; 568/9; 106/1.22, 1.25

[56] References Cited

U.S. PATENT DOCUMENTS

5,135,825  8/1992  Mori et al. .................... 429/124

*Primary Examiner*—Floyd D. Higel
*Attorney, Agent, or Firm*—Oblon, Spivak, McClelland, Maier & Neustadt, P.C.

[57] ABSTRACT

There are disclosed a process for preparing an ambient temperature molten salt, which comprises treating an ambient temperature molten salt consisting essentially of 20 to 50 mole % of an aluminum halide and 80 to 50 mole % of an onium halide, containing oxygen-containing impurities originating from water with thionyl chloride and a process for preparing an ambient temperature molten salt for effecting aluminum electroplating, which comprises treating mixed ambient temperature molten salts consisting essentially of 30 to 50 mole % of an aluminum halide and 70 to 50 mole % of an onium halide, containing oxygen-containing impurities originating from water with thionyl chloride, and then adding aluminum halide to the molten salt to prepare an ambient temperature molten salt composition consisting essentially of 50 to 80 mole % of an aluminum halide and 50 to 20 mole % of an onium halide.

4 Claims, No Drawings

PROCESS FOR PREPARING AN AMBIENT TEMPERATURE MOLTEN SALT USING THIONYL CHLORIDE

BACKGROUND OF THE INVENTION

1. Field of the Invention

The present invention relates to a process for preparing a high purity ambient temperature molten salt consisting essentially of an aluminum halide and an onium halide, and which is valuable in the field of using an ambient temperature molten salt, especially for efficiently effecting aluminum electroplating by using a plating bath comprising an ambient temperature molten salt.

2. Prior Art

It has been well known that an ambient temperature molten salt consisting of an aluminum halide and an onium halide is in a liquid state at an ambient temperature of an ordinary temperature and has high conductivity. Particularly, an ambient temperature molten salt consisting of an N,N'-dialkylimidazolium halide and an aluminum halide is greatly expected to be an electrolyte having novel characteristics which are extremely different from those of a conventional organic or inorganic electrolyte.

For example, a secondary battery using an ambient temperature molten salt comprising a 1,2,3-trialkylimidazolium halide and an alkyl halide as an electrolyte is proposed in Japanese Provisional Patent Publications No. 133669/1985 and No. 133670/1985. Also, a secondary battery using an ambient temperature molten salt comprising 1-ethyl- 3-methylimidazolium chloride and aluminum trichloride as an electrolyte is proposed in Japanese Provisional Patent Publication No. 165879/1987. Further, a secondary battery using an ambient temperature molten salt comprising a 1,3-dialkylimidazolium halide and a halide of a IIIb metal of the periodic table as an electrolyte is proposed in Japanese Provisional Patent Publication No. 136180/1985.

For preparing such an ambient temperature molten salt, it has been known a solid mixing method in which an aluminum halide and an onium halide which are each in a solid state are gradually mixed in a nitrogen-substituted gloved box (for example, ELECTROCHEMISTRY, vol. 54 (3), p. 257).

Recently, a method in which an aluminum halide is reacted with an onium halide in an inert solvent having a low boiling point (Japanese Provisional Patent Publication No. 24088/1991 which corresponds to U.S. Pat. No. 5,135,825 and EP-B1-0 404 179).

However, it has been extremely difficult to prepare a high purity ambient temperature molten salt in an industrial scale easily because the chemical materials used in these methods are hygroscopic.

On the other hand, the aluminum electroplating has been carried out by using a non-aqueous plating bath, particularly an organic solvent plating bath, because aluminum has a high affinity for oxygen and a standard electrode potential thereof is poor than that of hydrogen.

As the organic solvent plating bath, there may be exemplified those in which aluminum trichloride and either $LiAlH_4$ or $LiH$ are dissolved in an ether, and aluminum trichloride and $LiAlH_4$ are dissolved in tetrahydrofuran as representative examples (for example, D. E. Couch et al.; J. Electrochem., vol. 99 (6), p. 234). However, these plating baths each contain an extremely active $LiAlH_4$ or $LiH$ and therefore, if oxygen or water is present, $LiAlH_4$ or $LiH$ reacts with it to be decomposed, causing a problem that the current efficiency is lowered or that the life span of the bath is shortened. Such a plating bath also has a serious problem that the bath easily explodes or flames because an organic solvent used therein has a low flashing point.

As another example, a plating bath in which triethylaluminum and sodium fluoride are dissolved in toluene has been proposed (R. Suchentrunk; Z. WERKSTOFFTECH., vol. 12, p. 190). In this case, however, it is extremely difficult to deal with triethylaluminum having a high risk and it has been considered impossible to put such a plating bath into practical use.

Recently, a process for effecting aluminum electroplating has been proposed in Japanese Provisional Patent Publications No. 70592/1987, No. 272788/1989 and No. 272790/1989 in which a molten salt consisting of an aluminum halide and an onium halide is used as a plating bath. Such a plating bath, however, has a plating condition which easily changes in response to contamination with water, and even if the electroplating is carried out under constant conditions, a plating film having uniform quality cannot necessarily be obtained.

SUMMARY OF THE INVENTION

An object of the present invention is to solve the above problems by removing oxygen-containing impurities originating from water, and to provide a process for easily preparing a high purity ambient temperature molten salt consisting essentially of an aluminum halide and an onium halide in an industrial scale.

Another object of the present invention is to provide a process for preparing a high purity ambient temperature molten salt for an electroplating bath comprising an ambient temperature molten salt consisting essentially of an aluminum halide and an onium halide which can provide efficiently effecting aluminum electroplating and an aluminum plating film or coating which film always exhibits satisfactory plating states.

The inventors of the present invention have intensively studied to accomplish the above objects and found that a high purity ambient temperature molten salt can be easily prepared by treating an ambient temperature molten salt consisting essentially of an aluminum halide and an onium halide which consists essentially of oxygen-containing impurities originating from water with thionyl chloride.

The process for preparing an ambient temperature molten salt of the present invention comprises treating ambient temperature molten salts consisting essentially of 20 to 50 mole % of an aluminum halide and 80 to 50 mole % of an onium halide, containing oxygen-containing impurities originating from water with thionyl chloride; and then removing the oxygen-containing impurities together with the excessive amount of thionyl chloride.

The process for preparing an ambient temperature molten salt for effecting aluminum electroplating of the present invention comprises treating an ambient temperature molten salts consisting essentially of 30 to 50 mole % of an aluminum halide and 70 to 50 mole % of an onium halide, containing oxygen-containing impurities originating from water with thionyl chloride, then adding aluminum halide to the molten salt to prepare an ambient temperature molten salt composition consisting essentially of 50 to 80 mole % of an aluminum halide and 50 to 20 mole % of an onium halide.

DESCRIPTION OF THE PREFERRED EMBODIMENT

In the following, the present invention is explained in detail.

As the aluminum halide to be used in the present invention, there may be exemplified aluminum trichloride and aluminum tribromide. Among them, aluminum trichloride is most preferred.

As the onium halide to be used in the present invention, there may be exemplified a quaternary ammonium salt, for example; a tetra(lower alkyl)ammonium halide such as tetraethyl ammonium bromide, trimethylethyl ammonium chloride, etc.; a pyridinium salt such as a lower alkylpyridinium halide including butylpyridinium chloride. etc.; an imidazolium salt such as an N,N'-di(lower alkyl)imidazolium halide including 1-ethyl-3-methylimidazolium chloride, etc.; and a phosphonium salt such as a tetra(lower alkyl)phosphonium halide including ethyltributylphosphonium bromide, etc.

The aluminum halide and the onium halide may be mixed by the solid mixing method which is carried out by cooling a reactor or a mixing method using an inert solvent. The onium halide has a high hygroscopicity and thus sometimes contains water as impurities. In particular, when procedures for electroplating are repeated for a long time, the onium halide contained in a plating bath may contain water contained in a subject to be plated and/or a plating atmosphere as impurities. It has been known that the water is decomposed to form a hydrogen halide and oxygen-containing impurities during the procedures for mixing or electroplating. As the ambient temperature molten salt to be used in the present invention, a mixture consisting essentially of 20 to 50 mole % of an aluminum halide and 80 to 50 mole % of an onium halide is used. When the aluminum halide concentration is less than 30 mole % the ambient temperature molten salt has a undesirably high viscosity and it may be solidified, depending on the kind of the onium halide. When the aluminum halide concentration exceeds 50 mole %, the treatment with thionyl chloride described below will proceed with difficulty because of the strong hygroscopic nature of the aluminum halide. Therefore, an ambient temperature molten salt consisting essentially of 30 to 50 mole % of an aluminum halide and 70 to 50 mole % of an onium halide may preferably be treated with thionyl chloride.

The aluminum halide concentration of the molten salt before the treatment with thionyl chloride may be adjusted by adding an onium halide to the molten salt, for example, a plating bath generally used of the composition consisting essentially of 50 to 80 mole % of an aluminm halide and 50 to 20 mole % of an onium halide to prepare an ambient temperature molten salt consisting essentially of 30 to 50 mole % of an aluminum halide and 70 to 50 mole % of an onium halide.

The treatment with thionyl chloride may be carried out by adding thionyl chloride to the molten salt which contains oxygen-containing impurities to cause a reaction between oxygen-containing impurities and thionyl chloride resulting to volatilize sulfur dioxide; and removing the oxygen-containing impurities together with the excessive amount of thionyl chloride. The thionyl chloride may preferably be added in an amount of 0.1 to 2-fold moles based on the amount of the oxygen-containing impurities contained in the molten salt. If it is added in an amount of less than 0.1-fold mole, the oxygen-containing impurities cannot sufficiently be removed. If it is added in an amount of more than 2-fold moles, it will undesirably require more time and more energy to remove the excessive amount of thionyl chloride. The amount of the oxygen-containing impurities contained in the ambient temperature molten salt can be determined by measuring the absorption intensity of OH stretching frequency at a wave number of 3360 $cm^{-1}$ by an infrared spectrophotometer The reaction temperature is preferably in the range of a room temperature to 80° C. If the reaction temperature exceeds 80° C., thionyl chloride is undesirably distilled during the reaction. The reaction may proceed with addition of thionyl chloride and end within 5 hours after completion of the addition.

The oxygen-containing impurities are removed by distillation together with the excessive amount of thionyl chloride after termination of the reaction. Thionyl chloride can easily be removed by heating at less than 80° C. under reduced pressure. The amount of the remaining thionyl chloride may preferably be 5% by weight or less based on the weight of the ambient temperature molten salt. If the amount exceeds 5% by weight, the characteristics of the ambient temperature molten salt such as the aluminum electrodeposition characteristics are impaired and as a result, the aluminum plating cannot be carried out normally.

For the plating bath, after the treatment with thionyl chloride, an aluminum halide is added to prepare an ambient temperature molten salt composition consisting essentially of 50 to 80 mole % of an aluminum halide and 50 to 20 mole % of an onium halide and the electroplating is carried out by using the thus prepared molten salt composition.

The aluminum electroplating can be carried out with a high electrical efficiency by using an aluminum plate as an anode and a subject to be plated having conductivity as a cathode under the plating conditions of a direct current or a pulse current; a bath temperature of 0° to 150° C.; and a current density of 0.01 to 50 A/$dm^2$ so that uniform plating film or coating can be obtained. The plating may preferably be carried out under a dry inert gas atmosphere.

EXAMPLES

The present invention is described in detail by referring to Examples, Comparative examples and Referential example, but the scope of the invention is not limited by these Examples.

Example 1

To a glass reactor charged with 120 g of cyclohexane were added 147 g (1 mole) of 1-ethyl- 3-methylimidazolium chloride and 120 g (0.9 mole) of aluminum trichloride and the materials were mixed well. Then, the mixture is heated at 60° C. and cyclohexane was removed under reduced pressure (10 mmHg) by distillation. The thus obtained 267 g of the ambient temperature molten salt consisting essentially of 47 mole % of aluminum trichloride was revealed to contain 2 % by weight of oxygen-containing impurities originating from water by an IR spectrophotometer at a wave number of 3360 $cm^{-1}$.

When 53 g (0.45 mole) of thionyl chloride was added dropwise to the above ambient temperature molten salt, the mixture severely bubbled or foamed. The reactor was heated to 70° C. to allow the mixture to react for 4 hours, and then, the mixture was heated at 90° C. for 2 hours under reduced pressure of 10 mmHg to remove the excessive amount of thionyl chloride. The concentration. of thionyl chloride remaining in the ambient temperature molten salt was 0.3% according to an IR spectrophotometer at 1230 $cm^{-1}$.

To the ambient temperature molten salt after the treatment with thionyl chloride was added 147 g of aluminum trichloride (1.1 moles) so that a plating bath consisting essentially of 67 mole % of aluminum trichloride and 33 mole % of 1-ethyl-3-methylimidazolium chloride was prepared. The IR spectrophotometer at 3360 cm$^{-1}$ revealed that the plating bath contains an undetectable amount (less than detectable limit) of oxygen-containing impurities originating from water.

Comparative Example 1

The procedures were carried out in the same manner as in Example 1 except that 53 g of thionyl chloride was not added.

It was revealed by an IR spectrophotometer at a wave number of 3360 cm$^{-1}$ that the obtained ambient temperature molten salt was contaminated with 1% by weight of oxygen-containing impurities originating from water.

Comparative Example 2

The procedures were carried out in the same manner as in Example 1 except that an ambient temperature molten salt consisting essentially of 147 g (1 mole) of 1-ethyl-3-methylimidazolium chloride and 289 g (2 mole) of aluminum trichloride containing 2% by weight of oxygen-containing impurities was used and was treated with 89 g (0.75 mole) of thionyl chloride. The IR spectrophotometer at 3360 cm$^{-1}$ revealed that the obtained ambient temperature molten salt was contaminated with 2% by weight of oxygen-containing impurities originating from water.

Example 2

An ambient temperature molten salt was synthesized under a dry nitrogen atmosphere by mixing 147 g (1 mole) of 1-ethyl-3-methylimidazolium chloride and 289 g (2 moles) of aluminum trichloride to prepare an ambient temperature molten salt comprising 67 mole % of aluminum trichloride. To the thus prepared ambient temperature molten salt was added 9 g of water (2% by weight) to have 445 g of an ambient temperature molten salt. The molten salt is not suitable as a plating bath as shown in Referential example since it contains oxygen-containing impurities.

The molten salt was put into a glass reactor and 176 g (1.2 moles) of 1-ethyl-3-methylimidazolium chloride was added to reduce the aluminum trichloride concentration to 48 mole %.

Then, 89 g (0.75 moles) of thionyl chloride was gradually added dropwise to the molten salt, which caused severe bubbling or foaming. The reactor was heated to 70° C. and the mixture was allowed to react for 4 hours. The reactor was then heated at 90° C. for 2 hours under reduced pressure of 10 mmHg to remove the excessive amount of thionyl chloride by distillation. The concentration of thionyl chloride remaining in the molten salt was 0.3% by weight according to an IR spectrophotometer at a wave number of 1230 cm$^{-1}$.

Application Example 1

To the molten salt after the treatment with thionyl chloride obtained in Example 2 was added 320 g (2.4 moles) of aluminum trichloride to prepare a plating bath comprising an ambient temperature molten salt consisting essentially of 67 mole % of aluminum trichloride and 33 mole % of 1-ethyl-3-methylimidazolium chloride.

Electrolysis was carried out in this molten salt as a plating bath by using an aluminum plate as an anode and a copper plate as a cathode at 60° C. under the conditions of the direct current density of 5 A/dm$^2$ to have a white aluminum coating on the copper plate.

Referential Example

When electrolysis was carried out in the same manner as in Application example 1 by using the molten salt obtained in Comparative example 1, an aluminum coating was not formed on the copper plate and a surface thereof became black.

When electrolysis was carried out in the same manner as in Application example 1 by using the molten salt obtained in Comparative example 2, an aluminum coating was not formed on the copper plate and a surface thereof became black.

According to the present invention, an ambient temperature molten salt containing an aluminum halide and an onium halide which contains only a small amount of oxygen-containing impurities originating from water can be prepared. Further, a plating bath comprising an aluminum halide and an onium halide which contains only a small amount of oxygen-containing impurities originating from water can be regenerated. By using this highly purified molten salt, an aluminum coating can efficiently be obtained which always exhibits satisfactory conditions.

We claim:

1. A process for preparing an ambient temperature molten salt which comprises treating an ambient temperature molten salt consisting essentially of 20 to 50 mole % of aluminum trichloride and 80 to 50 mole % of a salt selected from the group consisting tetraethyl ammonium bromide, trimethylethyl ammonium chloride, butylpyridinium chloride, 1-ethyl-3-methyl imidazolium chloride, ethyltributyl phosphonium bromide, and a mixture thereof with thionyl chloride.

2. A process for preparing an ambient temperature molten salt which comprises adding a salt selected from the group consisting of tetraethyl ammonium bromide, trimethylethyl ammonium chloride, butylpyridinium chloride, 1-ethyl-3-methyl imidazolium chloride, ethyltributyl phosphonium bromide, and a mixture thereof to an ambient temperature molten salt consisting essentially of 50 to 80 mole % of aluminum trichloride and 50 to 20 mole % of a salt selected from the group consisting of tetraethyl ammonium bromide, trimethylethyl ammonium chloride, butylpyridinium chloride, 1-ethyl-3-methyl imidazolium chloride, ethyltributyl phosphonium bromide, and a mixture thereof to prepare an ambient temperature molten salt consisting essentially of 30 to 50 mole % of aluminum trichloride and 70 to 50 mole % of a salt selected of the group consisting of tetraethyl ammonium bromide, trimethylethyl ammonium chloride, butylpyridinium chloride, 1-ethyl-3-methyl imidazolium chloride, ethyltributyl phosphonium bromide, and a mixture thereof; and treating said molten salt with thionyl chloride.

3. The process for preparing an ambient temperature molten salt according to claim 2, wherein after treatment with thionyl chloride, aluminum trichloride is added to said molten salt such that an ambient temperature molten salt consisting essentially of 50 to 80 mole % of aluminum trichloride and 50 to 20 mole % of a salt selected from the group consisting of tetraethyl ammonium bromide, trimethylethyl ammonium chloride, butylpyridinium chloride, 1-ethyl-3-methyl imidazolium chloride, ethyltributyl phosphonium bromide, and a mixture thereof is obtained.

4. The process for preparing an ambient temperature molten salt according to claim 1, wherein the ambient temperature molten salt is treated with 0.1 to 2-fold moles of thionyl chloride based on the amount of the oxygen-containing impurities.

* * * * *